Figure 1:
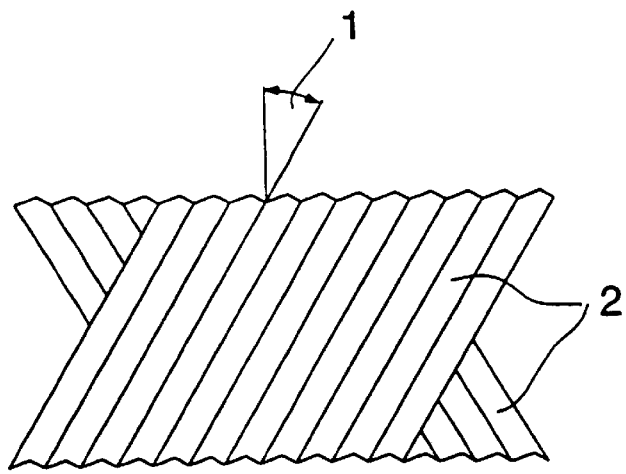

United States Patent [19]
Burst et al.

[11] Patent Number: 5,950,454
[45] Date of Patent: Sep. 14, 1999

[54] CLOTH OR CLOTH-LIKE PACKING WHICH IS SUBJECT TO LOW PRESSURE LOSSES AND HAS AN ORDERED STRUCTURE FOR USE IN MATERIAL-EXCHANGE COLUMNS AND RECTIFICATION METHOD USING SUCH PACKING

[75] Inventors: Wolfram Burst, Mannheim; Horst Hartmann, Böhl-Iggelheim; Wulf Kaiser, Bad Dürkheim; Harald Laas, Maxdorf; Paul Grafen, Weisenheim; Bernhard Bockstiegel, Römerberg; Kai-Uwe Baldenius, Frankenthal, all of Germany

[73] Assignee: BASF Aktiengesellschaft, Ludwigshafen, Germany

[21] Appl. No.: 08/973,875

[22] PCT Filed: Jun. 29, 1996

[86] PCT No.: PCT/EP96/02851

§ 371 Date: Jan. 7, 1998

§ 102(e) Date: Jan. 7, 1998

[87] PCT Pub. No.: WO97/02890

PCT Pub. Date: Jan. 30, 1997

[30] Foreign Application Priority Data

Jul. 8, 1995 [DE] Germany .............................. 195 24 928
Feb. 13, 1996 [DE] Germany .............................. 196 05 286

[51] Int. Cl.$^6$ .................................................. B01D 47/00
[52] U.S. Cl. ............................ 62/643; 62/906; 261/112.2
[58] Field of Search ..................... 62/643, 906; 261/100, 261/112.2

[56] References Cited

U.S. PATENT DOCUMENTS

| | | | |
|---|---|---|---|
| 4,186,159 | 1/1980 | Huber | 261/112.2 |
| 4,201,736 | 5/1980 | Ellis et al. | 261/98 |
| 4,296,050 | 10/1981 | Meier | 261/112.2 |
| 5,326,504 | 7/1994 | Gates | 261/112.1 |
| 5,407,607 | 4/1995 | Mix | 261/112.2 |
| 5,419,136 | 5/1995 | McKeigue | 62/906 X |
| 5,514,304 | 5/1996 | Riemer | 261/97 |
| 5,578,254 | 11/1996 | Mix | 261/112.2 |

*Primary Examiner*—Christopher B. Kilner
*Attorney, Agent, or Firm*—Oblon, Spivak, MClelland, Maier & Neustadt, P.C.

[57] ABSTRACT

Packing elements with a low pressure drop for mass transfer column internals of the internal diameter of the column and of a height of from 40 to 300 mm made of dimensionally stable layers, which have an ordered structure and are in mutual contact, of cloth material or cloth-like material with a specific surface area of from 100 to 2000 $m^2/m^3$, wherein a) the shaped layers of cloth material or cloth-like material, preferably made of metal cloth, which are in mutual contact are arranged so that they form a multiplicity of narrow flow channels, preferably virtually triangular, virtually rectangular or else virtually equilateral hexagonal flow channels, in which the angle of inclination of the serration of the individual cloth layers of the packing to the column axis is only 0 to 25°, preferably 3 to 14°, and b) to ensure mechanical stability of the packing elements, if necessary wires or thin rods are fixed in suitable arrangement between the cloth layers, or else the cloth layers are firmly connected at some points of contact, and processes for obtaining pure substances from substance mixtures by rectification using the novel packing elements.

10 Claims, 2 Drawing Sheets

CLOTH OR CLOTH-LIKE PACKING WHICH IS SUBJECT TO LOW PRESSURE LOSSES AND HAS AN ORDERED STRUCTURE FOR USE IN MATERIAL-EXCHANGE COLUMNS AND RECTIFICATION METHOD USING SUCH PACKING

Cloth packings or cloth-like packings with a low pressure drop and an ordered structure for use in mass transfer columns, and rectification using these packings.

The invention relates to packing elements for mass transfer columns and column internals formed therefrom, made of cloth material or cloth-like material, preferably of metal cloth, with an ordered structure and novel geometry for use in a mass transfer column with particularly low specific pressure drop, and to their use for the rectification of substance mixtures.

The workup of product mixtures by distillation generally affords the best results in the case of countercurrent distillation, also called rectification, ie. a distillation process in which the liquid flows downward as reflux and the vapor flows upward in the column. This results in enrichment of the more volatile components in the vapor and of the less volatile components in the liquid.

This mass and heat transport is intensified by elements fitted inside the column, such as column plates or packings, which ensure a sufficient contact time of the phases and a sufficiently large phase boundary area. However, these column internals, together with the reflux flowing downward result in a resistance to vapor flow in the column which is called the pressure drop. For a given column geometry, ie. diameter and column height, the pressure drop in a column depends not only on the nature and amount of the compounds to be rectified but also very strongly on the nature of the column internals.

Generally used for the fractionation of substance mixtures which require a high separation efficiency are rectification columns with internals made of metal cloth with an ordered structure. These cloth packings which are built up systematically in regular geometry and have defined areas for the countercurrent phases to pass through are distinguished from all other internals by the possibility of higher flow rates, a better separation effect and a lower specific pressure drop. They are therefore used in all vacuum rectifications in which, because of the temperature-sensitivity of the mixture to be separated, it is particularly important to limit the pressure drop in the column. Particularly suitable column packings are metal cloth packings of the BX and CY types supplied by Sulzer (cf. Sulzer company publication "Trennkolonnen für Destillation und Absorption") and metal cloth packings with a similar effect supplied by other companies, eg. Montz-Pak type A3 from Montz GmbH and cloth-like packings such as the BSH types of Montz GmbH.

A diagrammatic representation of such columns is to be found, for example, on page 103 of the textbook "Thermische Trennverfahren" by Klaus Sattler, VCH Verlagsges.mbH, Weinheim (FRG), 1988. Concerning further details of the rectification of substance mixtures, we refer to this textbook by Klaus Sattler, pages 101–225, in particular 120–160 and 199–214.

The thermal stressability of many high-boiling mixtures is so low that, despite the use of the described metal cloth packings or cloth-like packings with an ordered structure and overhead pressures in the column of only 0.5 to 1 mbar, the pressure drop at the cloth packings which are required for the necessary separation efficiency would result in bottom temperatures which are above the decomposition range for the compounds to be separated.

It is an object of the present invention to develop novel cloth packings or cloth-like packings with an ordered structure which, with the same separation efficiency, show an even lower pressure drop than all column internals available hitherto, ie. cloth packings which permit even high-boiling air- and/or temperature-sensitive substance mixtures which require a high separation efficiency to be separated by distillation with good yields without using alternative costly distillation processes, such as high vacuum distillation or short-path distillation, and novel cloth packings which, owing to their low pressure drop, very generally permit low bottom temperatures and thus distillation under milder conditions, or else increase the capacity of the column.

The invention relates to packing elements with a low pressure drop for mass transfer column internals of the internal diameter of the column and of a height of from 40 to 300 mm made of dimensionally stable layers, which have an ordered structure and are in mutual contact, of cloth material or cloth-like material with a specific surface area of from 100 to 2000 $m^2/m^3$ with novel geometry, wherein a) the shaped layers of cloth material or cloth-like material which are in mutual contact are arranged so that they form a multiplicity of narrow flow channels, preferably virtually triangular, virtually rectangular or else virtually equilateral hexagonal flow channels in which the angle of inclination of the serration of the individual cloth layers of the packing to the column axis is only 0 to 25°, preferably 3 to 14°, in particular 4–6°, and b) to ensure mechanical stability of the packing elements, if necessary wires or thin rods are fixed in suitable, preferably horizontal arrangement between the cloth layers, or else the cloth layers are firmly connected at some points of contact.

Thus, whereas the angle of inclination of the serration with conventional cloth packings is generally at least 30°, the cloth packings according to the invention which are formed from packing elements or disk-shaped column internals show an angle of inclination of the serration of the cloth layers to the column axis of only 0 to 25°, preferably 3 to 14°, in particular 4 to 6°. The angle of inclination of the serration of the cloth layers to the column axis is illustrated in FIG. 1. In this figure, 1 denotes the angle of inclination of the serration of the cloth layers to the column axis and 2 denotes the cloth layers.

As with known cloth packings, the individual shaped layers of cloth material or cloth-like material which are in mutual contact are arranged so that the flow channels which are formed alternately run in opposite directions when the angle of inclination of the serration of the individual cloth layers to the column axis is greater than 0 with the packing elements according to the invention or in the disk-shaped mass transfer column internals formed therefrom.

The invention also relates to disk-shaped mass transfer column internals of the particular internal diameter of the column and of a height of from 40 to 300 mm, consisting of one or a multiplicity of the packing elements according to the invention made of cloth material or cloth-like material, and column internals consisting of a multiplicity of disk-shaped mass transfer column internals according to the invention which are arranged one above the other, the disk-shaped column internals being rotated by about 90° relative to each other.

The packings formed from the novel packing elements or disk-shaped column internals have the lowest specific pressure drop of all the packings previously disclosed or described in the literature. The specific pressure drop is the pressure drop of the vapor flow when flowing through the cloth packing whose height corresponds exactly to one theoretical plate. With an F factor of 1√Pa, the specific pressure drops for the packings with a specific surface area of 500 m²/m³ which are currently on the market are, according to the manufacturers' statements, in the region of 0.09–0.11 mbar/$n_{th}$. The separation efficiency of these packings is about 5–7 plates per meter of packing. The use of the cloth packings according to the invention with flow channels which are vertical or only slightly inclined to the column axis has made it possible to reduce the specific pressure drop by about 50%, with comparable separation efficiency.

This makes it possible to extend the range of applications of mass transfer columns also to the rectification of high-boiling, air- and/or temperature-sensitive substances which require a high separation efficiency, because the bottom temperature can be considerably reduced owing to the reduction in the pressure drop.

It was extremely surprising that the cloth packings or cloth-like packings according to the invention with their flow channels which are vertical or inclined only slightly to the column axis show the same separation effect, with a considerably lower pressure drop, as the known cloth packings in which the angle of inclination of the serration of the individual cloth layers is at least 30° (cf. cloth packings BX, CY, DX and EX supplied by Sulzer Chemtech) and the angle of inclination of the undulating channels in the metal cloth packings of type A3 supplied by Montz is standardized at 30 or 45°, because it has previously been assumed that for optimal mass transfer, and thus for an optimal separation effect, besides good distribution of the liquid phase it is also necessary for the transverse mixing of the vapor phase to be optimal.

The only previously disclosed packing systems consisting of metal cloth packings with vertical flow channels are the Kloss and Neo-Kloss packings supplied by Montz GmbH. These packings consist of grooved or corrugated metal cloth layer strips which are wound spirally with spaces to form a wound element. They correspondingly contain long vertical annular flow slits at which the individual cloth layer strips do not make direct mutual contact. Although these packing systems have a lower pressure drop than the commercial cloth packings, they also have a lower separation efficiency. Their pressure drop per plate is therefore not less, ie. the specific pressure drop is not less.

The packing elements and column internals according to the invention with novel geometry can be produced by using all materials which are suitable for producing cloths and customary for producing cloths. The most important which may be mentioned are metal cloths made of stainless steels, such as those complying with DIN 1.0330; 1.4000; 1.4301; 1.4401; 1.4404; 1.4435; 1.4439; 1.4571 or the like, of Hasteloy C4, of aluminum (eg. DIN 3.0255), of copper, of titanium (eg. DIN 3.7025), of monel, of synthetic material such as polypropylene/polyacrylonitrile blended fabric or cloth made of glass fibers or carbon fibers. Cloth packings with a specific surface area of about 100 to 2000 m²/m³, preferably 250 to 1000 m²/m³, are advantageously used. Cloth packings formed from shaped metal cloth layers in mutual contact are preferred.

Figure 2A:
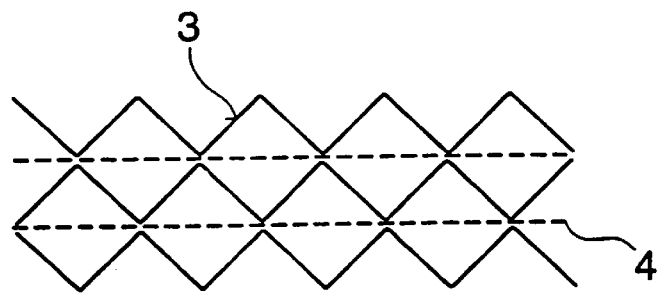
Figure 2B:
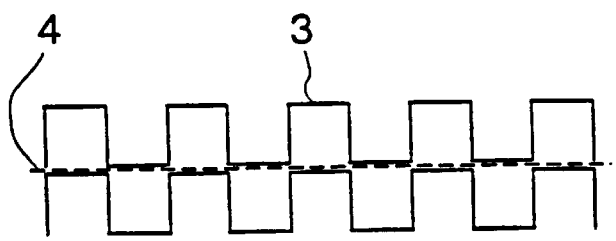
Figure 2C:
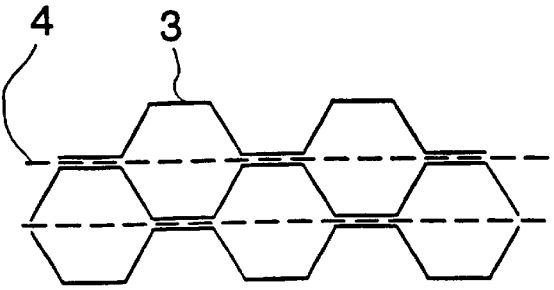

The cloth can be shaped in a conventional way. It takes place, for example, with formation of the shapes depicted in FIG. 2A), B) and C), in which the full lines represent a top view of the individual cloth layers, and the broken lines represent a top view of the wires or rods ensuring stability. In FIGS. 2A, 2B and 2C, 3 denotes the cloth layers and 4 denotes the wires or rods. Particularly advantageous packings are those in which grooved cloth layers (as shown in FIG. 2A) form the flow channels.

To ensure the mechanical stability of the packing elements, wires or thin rods, preferably metal wires or thin metal rods, with a diameter of preferably about 1 mm are fixed in a suitable, preferably horizontal, arrangement between the individual cloth layers, with the intention of preventing the cloth layers slipping into one another. However, the mechanical stability of packing elements can also be ensured by firmly connecting the individual cloth layers at a few points of contact, for example by soldering, welding or bonding.

The precondition for a good separation efficiency of the packings according to the invention is, as with all packings, a good liquid distribution underneath the inlet or removal points. Very good liquid distributors with a large number of drip points per cross-sectional area of the column are commercially obtainable for this purpose. It is also advantageous for good liquid distribution, especially in columns on an industrial scale, for one or more, preferably 2 or 3, disk-shaped packing internals with the larger angle of inclination of the serration of the cloth layers which has been customary hitherto to be fixed directly beneath the liquid distributor, and only then to arrange the column internals formed from the packing elements according to the invention underneath.

The cloth packings with an ordered structure which are normally used for rectifications consist of a number of disk-shaped column internals (packing layers) about 15 to 25 cm high which is appropriate for the required separation efficiency. One packing layer generally consists of a multiplicity of single shaped cloth layers of appropriate height. When fitted in the column, each packing layer is fitted at 90° in each case relative to the preceding one in order to ensure that mass distribution is as good as possible.

The packing elements according to the invention also are or form disk-shaped mass transfer column internals (packing layers) which, when fitted in the column, are rotated by about 90° in each case relative to the preceding packing layer. The height of the packing can be from 4 to 30, preferably 16 to 20, in particular 16 to 17 cm.

With an F factor of about 1 √Pa, the pressure drops for the packings with a specific surface area of 500 m²/m³ which are currently on the market are, according to the manufacturers' statements, in the region of 0.09 to 0.11 mbar per theoretical plate ($n_{th}$). The separation efficiency of these packings is about 5–7 plates per meter of packing. The use of the cloth packings according to the invention with flow channels which are vertical or only slightly inclined to the column axis has made it possible to reduce the specific pressure drop by about 50%, with comparable separation efficiency, resulting in considerable increases in the capacity of the column or else making it possible to use columns of smaller diameter.

The invention accordingly also relates to a process for obtaining pure substances from substance mixtures by rectification of these substance mixtures, which is done by using rectification columns in which all or at least part of the disk-shaped column internals are formed from the packing elements according to the invention, or, for columns of small diameter and/or columns into which cloth packings can readily be introduced from above, are disk-shaped packing elements of this type.

The low specific pressure drop of the novel packings makes it possible to extend the range of application of mass transfer columns also to the rectification of mixtures of high-boiling air- and/or temperature-sensitive substances which require a high separation efficiency under medium vacuum, ie. under pressues from about 0.1 to 2.5 mbar, because the bottom temperature can be considerably reduced owing to the reduction in the pressure drop.

The invention accordingly also relates to a process for obtaining pure substances from mixtures of high-boiling air- and/or temperature-sensitive substances which require a high separation efficiency, by rectification under medium vacuum in a column containing metal cloth packings with an ordered structure, wherein the rectification is carried out in a column a) in which the liquid distribution is carried out by channel distributors with 500 or more drip points per $m^2$, b) in which the channels of the liquid distributors are arranged at an angle of about 90° to the cloth layers of the disk-shaped column internals located immediately below these distributors, c) in which two or more disk-shaped column internals which have a height of only from 20 to 100 mm and whose cloth layers are rotated by 90° relative to each other are fitted below the liquid distributors, d) in which all other or some of the other disk-shaped column internals are formed from the packing elements according to the invention, e) wherein the columns are designed so that no heat exchange can take place through the column wall during the rectification, and f) wherein the column is designed in the case of air-sensitive substances so that it can be operated virtually with exclusion of air.

An example which may be mentioned of a mixture of high-boiling and highly air- and/or temperature-sensitive substances requiring a high separation efficiency is synthetic vitamin E acetate (VEA), which is prepared industrially by reacting trimethylhydroquinone with phytol or isophytol and subsequently esterifying with acetic anhydride and still contains small amounts of colored lower-boiling and higher-boiling impurities. Since VEA is increasingly being used for human nutrition and health preservation, the requirements for the purity of this product are becoming increasingly great. Rectification, which is generally very advantageous for purifying products on the industrial scale, is very difficult in the case of VEA due to its high boiling point together with its instability at elevated temperatures. This is why to date essentially distillations under high vacuum or even molecular distillations have been carried out in order to be able to distil VEA at the lowest possible temperatures.

However, since distillations under high vacuum, but especially molecular distillations, while giving high purities not only have the disadvantage of low distillation yields but are also extremely complex and therefore very costly in terms both of the capital costs and of the operating costs, the novel packing elements and column internals are particularly important for final purification of VEA, ie. in the case of rectification of VEA which is contaminated with colored lower-boiling and higher-boiling substances as a mixture of high-boiling air- and/or temperature-sensitive substances.

Feature a) of the claim relating thereto claims liquid distribution with channel distributors with 500 or more drip points. Similar distributors, which are also called capillary distributors but are round, are marketed by Sulzer and by Montz and are described, for example, in EP 512 277. Known channel distributors generally have only 50 to 60 drip points per $m^2$.

The use according to the invention of the channel distributors reduces the pressure drop in two different ways. They cause, on the one hand, a rapid and extremely fine distribution and thus, in the final analysis, better utilization of the packing for distributing the mixture to be separated and, on the other hand, a very low dripping density.

However, in order to achieve an optimal separation efficiency, it is not only a large number of drip points but also the arrangement of the distributors relative to the packing elements which is important.

One layer of a cloth packing generally consists of a multiplicity of, normally single, cloth layers with a height of 170 mm. On fitting, each packing layer is fitted at 90° relative to the preceding one. The arrangement of the distributors is, according to feature b), likewise rotated by 90° relative to the packing element located immediately below the distributors, or to the packing layer located there.

The liquid then spreads out on one of these cloth layers at a particular angle. After an inflow length which depends on the angle of spread and the distance between two drip points, a uniform film has formed over one cloth layer.

Optimal utilization of the packing, ie. fastest possible distribution of the liquid on all the cloth layers, is achieved when the packing is rotated by 90° at this point.

Beneath the liquid distributors, according to feature c), 2 or more packing elements with a height of only from 20 to 100 mm, preferably 25 to 50 mm, in particular 35 to 45 mm, are inserted with their cloth layers rotated by 90° relative to each other. The separation of the packing into elements with a smaller height makes it possible to achieve the fastest possible distribution and thus optimal utilization of the packing for separation.

According to feature f), the rectification is, if necessary, to be carried out virtually with exclusion of air. This is particularly important for air-sensitive substance mixtures, as in the case of crude vitamin E acetate. The use of newly developed, particularly efficient sealing materials such as Helicoflex® supplied by Cefilac for sealing flanges and/or ports for equipment for process supervision is therefore absolutely necessary. It is particularly advantageous to seal flanges by using welded lip seals as described, for example, in German Patents DE 27 10 859, DE 39 12 478 or DD 44 07 728.

Only small substance streams circulate in medium-vacuum rectification columns. Therefore any loss of heat immediately results in uncontrolled condensation on the column wall, which reduces the separation efficiency of the column. The prevention, required by feature e), of heat exchange through the column wall can best be ensured by a combination of insulation and protective heating of the column. Industrial implementation of such protective heating is advantageously achieved in the following way: a metal plate jacket is attached to a first insulating layer on the column casing. This metal plate jacket is again insulated. Another metal plate jacket and the heating are then attached to this insulating layer and finally insulated to the outside. The heating is then controlled by making the temperature difference between the column casing and the first metal plate jacket zero.

Because of the thermal instability, VEA can be rectified in packed columns with a maximum height of 5 m when known cloth packings are used.

When the column internals according to the invention are used, owing to the reduction in the pressure drop it is also possible to employ packed columns with a height of more than 5 m for final purification of VEA by distillation.

The following example with comparative example is intended to show the great advantage of the packings with novel geometry according to the invention.

Comparison of the specific pressure drop $\Delta p/n_{th}$ of a metal cloth packing according to the invention with that of a known metal cloth packing of the same specific surface area.

A laboratory column with a diameter of 45 mm and a length of 1.8 m was packed in each case 1) for comparison with a commercial metal cloth packing of Montz type A 3-500 with a specific surface area of 500 $m^2/m^3$ and an angle of inclination of the undulating channels of 30° to the column axis and 2) with a metal cloth packing according to the invention with a specific surface area of 500 $m^2/m^3$ and an angle of inclination of the serration of the individual cloth layers of the packing to the column axis of 5°.

The liquid distribution took place in both cases with one drip point, and the overhead pressure was 50 mbar. A chlorobenzene/ethylbenzene mixture was used as test system. The specific pressure drop ($\Delta p/n_{th}$) with an F factor of from 0.5 to about 2 was determined, and the results have been plotted in FIG. 3.

Figure 3:
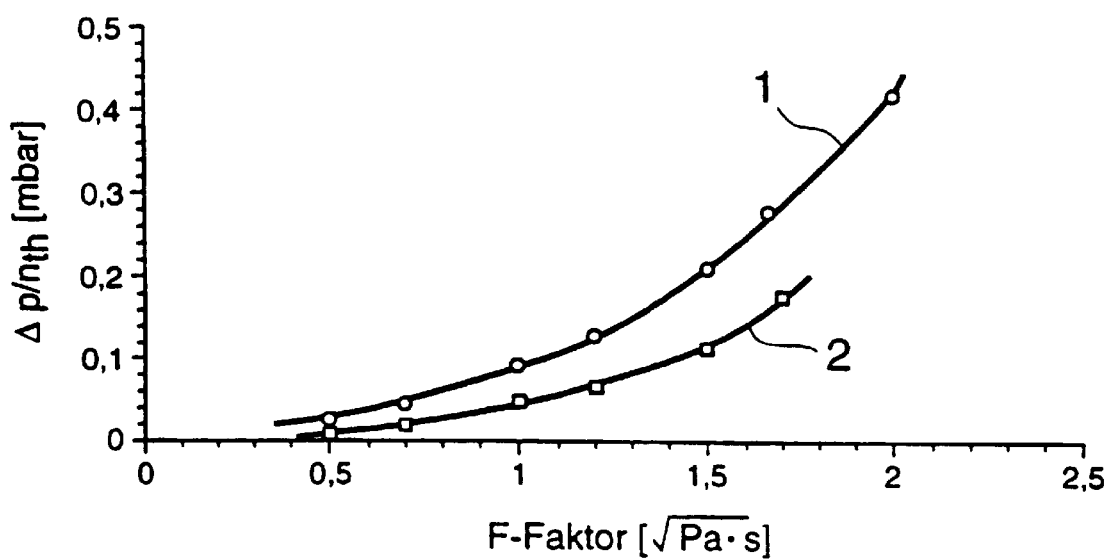

In FIG. 3, curve 1 represents the pressure drop for the Montz type A3 cloth packing (comparison) and curve 2 represents the pressure drop for the metal cloth packing according to the invention.

The curves show that the packing according to the invention displays a considerably smaller specific pressure drop. In the range from F=0.5 to 2 $\sqrt{Pa}$, the specific pressure drop is only about half that with the Montz type A 3-500 cloth packing with the same separation effect.

We claim:

1. Packing elements with a low pressure drop for mass transfer column internals of the internal diameter of the column and of a height of from 40 to 300 mm made of dimensionally stable layers, which have an ordered structure and are in mutual contact, of cloth material or cloth-like material with a specific surface area of from 100 to 2000 $m^2/m^3$, wherein
    a) the shaped layers of cloth material or cloth-like material which are in mutual contact are arranged so that they form a multiplicity of narrow flow channels in which the angle of inclination of the serration of the individual cloth layers to the column axis is 0 to 15°, and
    b) to ensure mechanical stability of the packing elements, if necessary wires or thin rods are fixed in suitable arrangement between the cloth layers, or else the cloth layers are firmly connected at some points of contact.

2. Packing elements for mass transfer column internals as claimed in claim 1, wherein the angle of inclination of the serration of the individual cloth layers of the packing elements to the column axis is 3 to 14°.

3. Packing elements for mass transfer column internals as claimed in claim 1, wherein the structured layers in mutual contact are formed from metal cloth or cloth-like material made of metal.

4. Packing elements for mass transfer column internals as claimed in claim 1, wherein, to ensure mechanical stability of the packing elements, wires or rods are fixed in horizontal arrangement between the individual cloth layers.

5. Packing elements for mass transfer column internals as claimed in claim 1, wherein the shaped layers of cloth material or cloth-like material which are in mutual contact are arranged so that they form virtually triangular, virtually rectangular or else virtually equilateral hexagonal flow channels.

6. Packing elements for mass transfer column internals as claimed in claim 1, wherein the shaped layers of cloth material or cloth-like material which are in mutual contact are arranged so that the flow channels formed by them alternately run in opposite directions when the angle of inclination of the serration of the individual cloth layers to the column axis is greater than 0.

7. Disk-shaped mass transfer column internals of the internal diameter of the column and of a height of from 40 to 300 mm consisting of one or a multiplicity of packing elements made of dimensionally stable layers of cloth material or cloth-like material which have an ordered structure and are in mutual contact, as claimed in claim 1.

8. Column internals consisting of a multiplicity of disc-shaped mass transfer column internals as claimed in claim 7, which are arranged one above the other, where the disc-shaped column internals are rotated by about 90° relative to each other.

9. A process for obtaining pure substances from substance mixtures by rectification of these substance mixtures, which comprises using for this purpose rectification columns in which all or at least part of the disc-shaped column internals are formed from packing elements as claimed in claim 1, or are such.

10. A process for obtaining pure substances from mixtures of high-boiling air- and/or temperature-sensitive substances which require a high separation efficiency, by rectification under medium vacuum in columns containing metal cloth packings with an ordered structure, which comprises carrying out the rectification in a column
    a) in which the liquid distribution is carried out by channel distributors with 500 or more drip points per $m^2$,
    b) in which the channels of the liquid distributors are arranged at an angle of about 90° to the cloth layers of the disc-shaped column internals located immediately below these distributors,
    c) in which two or more disc-shaped column internals which have a height of only from 20 to 100 mm and whose cloth layers are rotated by 90° relative to each other are fitted below the liquid distributors,
    d) in which all other or some of the other disc-shaped column internals are formed from packing elements as claimed in claim 1,
    e) wherein the columns are designed so that no heat exchange can take place through the column wall during the rectification, and
    f) wherein the column is designed in the case of air-sensitive substances so that it can be operated virtually with exclusion of air.

* * * * *